US007261867B1

(12) United States Patent
Sandford et al.

(10) Patent No.: US 7,261,867 B1
(45) Date of Patent: Aug. 28, 2007

(54) PRODUCTION OF SILVER SULFATE GRAINS USING ORGANO-SULFATE OR ORGANO-SULFONATE ADDITIVES

(75) Inventors: David W. Sandford, Rochester, NY (US); Thomas N. Blanton, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 11/399,754

(22) Filed: Apr. 7, 2006

(51) Int. Cl.
 *C01B 17/96* (2006.01)
 *C01G 5/00* (2006.01)

(52) U.S. Cl. .................. 423/45; 423/544; 423/548; 423/549; 423/266; 423/265; 424/618; 524/423; 524/543

(58) Field of Classification Search ............. 423/544, 423/548, 549, 45, 266, 265; 424/618; 524/423, 524/543
See application file for complete search history.

(56) References Cited

U.S. PATENT DOCUMENTS

| | | | |
|---|---|---|---|
| 4,140,748 A * | 2/1979 | Ore ....................... 423/157.4 |
| 4,525,410 A | 6/1985 | Hagiwara et al. |
| 4,728,323 A | 3/1988 | Matson |
| 5,049,140 A | 9/1991 | Brenner et al. |
| 5,064,599 A | 11/1991 | Ando et al. |
| 5,180,402 A | 1/1993 | Kubota et al. |
| 5,496,860 A | 3/1996 | Matsumoto et al. |
| 5,880,044 A | 3/1999 | Shimiz |
| 5,888,526 A | 3/1999 | Tsubai et al. |
| 6,248,342 B1 * | 6/2001 | Trogolo et al. ............ 424/404 |
| 6,274,519 B1 * | 8/2001 | Omori et al. ............. 442/229 |
| 6,436,420 B1 * | 8/2002 | Antelman ................ 424/404 |
| 6,479,144 B2 | 11/2002 | Petrea et al. |
| 6,585,843 B2 | 7/2003 | Nickell et al. |
| 2003/0215521 A1 * | 11/2003 | Laridon et al. ........... 424/604 |
| 2004/0009227 A1 * | 1/2004 | Yao ....................... 424/486 |

FOREIGN PATENT DOCUMENTS

| | | | |
|---|---|---|---|
| GB | 1082653 | | 9/1967 |
| JP | 03-271208 | | 3/1991 |
| JP | 02-841115 | | 4/1992 |
| JP | 5-85726 A | * | 4/1993 |
| JP | 08-133918 | | 5/1996 |
| WO | WO 2005/080488 | | 9/2005 |

OTHER PUBLICATIONS

"Oligodynamic Metals" by I.B. Romans in *Disinfection, Sterilization and Preservation*, (1968).
"The Oligodynamic Effect of Silver" by A. Goetz et al. in *Silver In Industry*, (1940).
Th W. Richards et al, *Z. anorg. Allg. Chem.* 55, 72 (1907).
O. Honigschmid et al, *Z. anorg. Allg. Chem.* 195, 207 (1931).
H. Hahn et al, *Z. anorg. Allg. Chem.* 258, 91 (1949).
J.A. Spadaro et al. (Clinical Orthopaedics and Related Research, 143, pp. 266-270, 1979).
*The Pharmacological Basis of Therapeutics*; Sixth Ed.; (1980); Chapter 41; "Antiseptics and Disinfectants; Fungicides; Ectoparasiticides"; pp. 964-987; by S.C. Harvey.
*The Pharmacological Basis of Therapeutics*; Fifth Ed.; (1975); Chapter 46; "Heavy Metals"; pp. 924-945; by S.C. Harvey.

* cited by examiner

*Primary Examiner*—Timothy C. Vanoy
(74) *Attorney, Agent, or Firm*—Andrew J. Anderson

(57) ABSTRACT

An aqueous precipitation process for the preparation of particles comprising primarily silver sulfate, comprising reacting an aqueous soluble silver salt and an aqueous soluble source of inorganic sulfate ion in an agitated precipitation reactor vessel and precipitating particles comprising primarily silver sulfate, wherein the reaction and precipitation are performed in the presence of an aqueous soluble organo-sulfate or organo-sulfonate additive compound, the amount of additive being a minor molar percentage, relative to the molar amount of silver sulfate precipitated, and effective to result in precipitation of particles comprising primarily silver sulfate having a mean grain size of less than 50 micrometers.

20 Claims, No Drawings

PRODUCTION OF SILVER SULFATE GRAINS USING ORGANO-SULFATE OR ORGANO-SULFONATE ADDITIVES

FIELD OF THE INVENTION

The present invention relates to the production of silver sulfate particles produced by aqueous precipitation methods, and in particular micron sized silver sulfate particles produced with uniform size employing organo-sulfate or organo-sulfonate additives, and the use thereof as an antimicrobial and antiviral agent in polymeric materials.

BACKGROUND OF THE INVENTION

There are various uses for silver sulfate, including as a synthetic reagent; a source of silver in the preparation of catalysts, plastic composite materials and various platinum complexes; as well as a source of silver in some photographic processes. Recently silver sulfate has been incorporated into plastics and facial creams as an antimicrobial and antifungal agent. To satisfy the demands of more modern applications, reduction of particle sizes of materials to the micron and nanometer size ranges is often required to take advantage of the higher surface area, surface energy, reactivity, dispersibility, uniformity and smoothness of coatings made thereof, optical clarity due to reduced light scatter, etc., inherent in these forms of matter. In addition, with the miniaturization of the physical size of many objects and devices, a similar limitation on the physical size of material components is now commonly encountered.

Silver sulfate is a commercially available material that is produced by conventional aqueous precipitation methods. The reaction of equimolar amounts of aqueous solutions of silver nitrate and sulfuric acid to from silver sulfate was described by Th. W. Richards and G. Jones, *Z. anorg. Allg. Chem.* 55, 72 (1907). A similar precipitation process using sodium sulfate as the source of sulfate ion was reported by O. Honigschmid and R. Sachtleben, *Z. anorg. Allg. Chem.* 195, 207 (1931). An alternate method employing the immersion of silver metal in a sulfuric acid solution was also reported by O. Honigschmid and R. Sachtleben (loc. cit.). Precipitation of finely divided silver sulfate from an aqueous solution via the addition of alcohol was later reported by H. Hahn and E. Gilbert, *Z. anorg. Allg. Chem.* 258, 91 (1949). Silver salts are widely known to be thermally and photolytically unstable, discoloring to form brown, gray or black products. Silver ion may be reduced to its metallic state, or oxidized to silver oxide, or react with sulfur to form silver sulfide. Silver sulfate has been observed to decompose by light to a violet color.

The antimicrobial properties of silver have been known for several thousand years. The general pharmacological properties of silver are summarized in "Heavy Metals"—by Stewart C. Harvey and "Antiseptics and Disinfectants: Fungicides; Ectoparasiticides"—by Stewart Harvey in *The Pharmacological Basis of Therapeutics*, Fifth Edition, by Louis S. Goodman and Alfred Gilman (editors), published by MacMillan Publishing Company, NY, 1975. It is now understood that the affinity of silver ion to biologically important moieties such as sulfhydryl, amino, imidazole, carboxyl and phosphate groups are primarily responsible for its antimicrobial activity.

The attachment of silver ions to one of these reactive groups on a protein results in the precipitation and denaturation of the protein. The extent of the reaction is related to the concentration of silver ions. The diffusion of silver ion into mammalian tissues is self-regulated by its intrinsic preference for binding to proteins through the various biologically important moieties on the proteins, as well as precipitation by the chloride ions in the environment. Thus, the very affinity of silver ion to a large number of biologically important chemical moieties (an affinity which is responsible for its action as a germicidal/biocidal/viricidal/fungicidal/bacteriocidal agent) is also responsible for limiting its systemic action—silver is not easily absorbed by the body. This is a primary reason for the tremendous interest in the use of silver containing species as an antimicrobial, i.e., an agent capable of destroying or inhibiting the growth of microorganisms, such as bacteria, yeast, fungi and algae, as well as viruses. In addition to the affinity of silver ions to biologically relevant species that leads to the denaturation and precipitation of proteins, some silver compounds, those having low ionization or dissolution ability, also function effectively as antiseptics. Distilled water in contact with metallic silver becomes antibacterial even though the dissolved concentration of silver ions is less than 100 ppb. There are numerous mechanistic pathways by which this oligodynamic effect is manifested, i.e., ways in which silver ion interferes with the basic metabolic activities of bacteria at the cellular level to provide a bactericidal and/or bacteriostatic effect.

A detailed review of the oligodynamic effect of silver can be found in "Oligodynamic Metals" by I. B. Romans in *Disinfection, Sterilization and Preservation*, C. A. Lawrence and S. S. Bloek (editors), published by Lea and Fibiger (1968) and "The Oligodynamic Effect of Silver" by A. Goetz, R. L. Tracy and F. S. Harris, Jr. in *Silver in Industry*, Lawrence Addicks (editor), published by Reinhold Publishing Corporation, 1940. These reviews describe results that demonstrate that silver is effective as an antimicrobial agent towards a wide range of bacteria, and that silver can impact a cell through multiple biochemical pathways, making it difficult for a cell to develop resistance to silver. However, it is also known that the efficacy of silver as an antimicrobial agent depends critically on the chemical and physical identity of the silver source. The silver source can be silver in the form of metal particles of varying sizes, silver as a sparingly soluble material such as silver chloride, silver as a moderately soluble salt such as silver sulfate, silver as a highly soluble salt such as silver nitrate, etc. The efficiency of the silver also depends on i) the molecular identity of the active species—whether it is $Ag^+$ ion or a complex species such as $(AgSO_4)^-$, etc., and ii) the mechanism by which the active silver species interacts with the organism, which depends on the type of organism. Mechanisms can include, for example, adsorption to the cell wall which causes tearing; plasmolysis where the silver species penetrates the plasma membrane and binds to it; adsorption followed by the coagulation of the protoplasm; or precipitation of the protoplasmic albumin of the bacterial cell. The antibacterial efficacy of silver is determined, among other factors, by the nature and concentration of the active species, the type of bacteria; the surface area of the bacteria that is available for interaction with the active species, the bacterial concentration, the concentration and/or the surface area of species that could consume the active species and lower its activity, and the mechanisms of deactivation.

One proposed use of silver based antimicrobials is for textiles. Various methods are known in the art to render antimicrobial properties to a target fiber. The approach of embedding inorganic antimicrobial agents, such as zeolites, into low melting components of a conjugated fiber is described in U.S. Pat. No. 4,525,410 and U.S. Pat. No.

5,064,599. In another approach, the antimicrobial agent can be delivered during the process of making a synthetic fiber such as those described in U.S. Pat. No. 5,180,402, U.S. Pat. No. 5,880,044, and U.S. Pat. No. 5,888,526, or via a melt extrusion process as described in U.S. Pat. No. 6,479,144 and U.S. Pat. No. 6,585,843. In still yet another process, an antimicrobial metal ion can be ion exchanged with an ion exchange fiber as described in U.S. Pat. No. 5,496,860.

High-pressure laminates containing antimicrobial inorganic metal compounds are disclosed in U.S. Pat. No. 6,248,342. Deposition of antimicrobial metals or metal-containing compounds onto a resin film or target fiber has also been described in U.S. Pat. No. 6,274,519 and U.S. Pat. No. 6,436,420.

In particular, the prior art has disclosed formulations that are useful for highly soluble silver salts having aqueous solubility products, herein referred to as pKsp, of less than 1. Generally, these silver salts require the use of hydrophobic addenda to provide the desired combinations of antimicrobial behavior and durability. Conversely, it is also know that very insoluble metallic silver particles, having a pKsp greater than 15, would require hydrophilic addenda to provide the desired combinations of antimicrobial behavior and durability. There exists a need to provide sparingly soluble silver salts in the range of pKsp from about 3-8, which can be highly efficient in antimicrobial and antiviral behavior when incorporated directly into plastics and polymeric materials.

Parasiticidal preparations of metal alkylsulphates and metal detergent sulphonates are described by Duperray in GB 1,082,653. Disclosures include the preparation of silver salts of alkylsulphates (specifically, silver laurylsulfphate and silver lauroylamino-ethylsulphate) and the silver salt of an alkylarylsulphonate (specifically, silver dodecylbenzenesulphonate). These compounds are prepared by reacting an excess of the alkylsulphate or alkylarylsulphonate with silver hydroxide, to form a neutral salt (or 1:1 adduct). While considerable efficacy in destroying parasitic protozoa such as coccidiae and histomones resulted when these compounds were added to the drinking water of diseased chickens, turkeys and cattle, neutral silver salts of these kinds contain too much organic character for use in some applications. Specifically, silver laurylsulphate has been observed to be extremely discolored when added into even a relatively low temperature (about 170° C.) melt of a polyolefin. This result is typical of polymer melt additives that either contain too much unstable organic character or are simply added in an excessive amount.

An antimicrobial masterbatch formulation is disclosed in JP 2841115B2 wherein a silver salt and an organic antifungal agent are combined in a low melting wax to form a masterbatch with improved dispersibility and handling safety. More specifically, silver sulfate was sieved through a 100 mesh screen (particles sizes less than about 149 microns), combined with 2-(4-thiazolyl)benzimidazole and kneaded into polyethylene wax. This masterbatch material was then compounded into polypropylene, which was subsequently injection molded into thin test blocks. These test blocks were reported to be acceptable for coloration and thermal stability, while exhibiting antibacterial properties with respect to *E. coli* and *Staphylococcus*, and antifungal properties with respect to *Aspergillus niger*. Similar masterbatches are also described in JP 03271208, wherein a resin discoloration-preventing agent (e.g. UV light absorbent, UV light stabilizer, antioxidant) is also incorporated.

An antimicrobial mixture of zinc oxide and silver sulfate on an inorganic powder support is disclosed in JP 08133918, wherein the inorganic powder support is selected from calcium phosphate, silica gel, barium sulfate and titanium oxide. The average primary particle diameter of the inorganic carrier powder is preferably $\leq 10$ microns, more preferably $\leq 5$ microns. The amount of silver sulfate supported is $\geq 0.04\%$ and <5.0%, especially preferably $\geq 0.3\%$ and <1.8%. The ratio of zinc oxide to the inorganic powder supporting silver sulfate is selected from the range of 0.2:99.8 to 30:70. The low overall content of antimicrobially active silver sulfate (<5.0%) in these particulate mixtures requires a relatively high loading of the mixture into a polymer or other substrate.

Silver sulfate has been proposed as an antimicrobial agent in a number of medical applications. Incorporation of inorganic silver compounds in bone cement to reduce the risk of post-operative infection following the insertion of endoprosthetic orthopaedic implants was proposed and studied by J. A. Spadaro et al (Clinical Orthopaedics and Related Research, 143, 266-270, 1979). Silver chloride, silver oxide, silver sulphate and silver phosphate were incorporated in polymethylmethacrylate bone cement at 0.5% concentration and shown to significantly inhibit the bacterial growth of *Staphylococcus aureus, Escherichia coli* and *Pseudomonas aeruginosa*. Antimicrobial wound dressings are disclosed in U.S. Pat. No. 4,728,323; wherein a substrate is vapor or sputter coated with an antimicrobially effective film of a silver salt, preferably silver chloride or silver sulfate. An antimicrobial fitting for a catheter is disclosed in U.S. Pat. No. 5,049,140; wherein a proposal to fabricate a tubular member composed of a silicone/polyurethane elastomer in which is uniformly dispersed about 1 to 15% wt. of an antimicrobial agent, preferably silver sulfate, is described. A moldable plastic composite comprising cellulose and a urea/formaldehyde resin is disclosed in WO2005080488A1, wherein a silver salt, specifically silver sulfate, is incorporated to provide a surface having antiviral activity against SARS (severe acute respiratory syndrome) coronavirus.

Despite various references to the proposed use of silver salts as antimicrobial agents in various fields as referenced above, there are limited descriptions with respect to approaches in the prior art for preparing silver salts, specifically silver sulfate, of sufficiently small grain size and of optimal grain size distribution as may be desired for particular applications. A need exists, in particular, to provide antimicrobial agents such as silver salts, more specifically silver sulfate, in controlled particular sizes for use in plastics and polymer containing materials with improved antimicrobial efficacy, reduced discoloration and cost, that enable more robust manufacturing processes. A process of preparing silver sulfate with improved thermal stability is further desired. There is further a need for improved processes that are simple and cost effective.

SUMMARY OF THE INVENTION

In accordance with one embodiment, the present invention is directed towards a process comprising reacting an aqueous soluble silver salt and an aqueous soluble source of inorganic sulfate ion in an agitated precipitation reactor vessel and precipitating particles comprising primarily silver sulfate, wherein the reaction and precipitation are performed in the presence of an aqueous soluble organo-sulfate or organo-sulfonate additive compound, the amount of additive being a minor molar percentage, relative to the molar amount of silver sulfate precipitated, and effective to result in precipitation of particles comprising primarily silver sulfate having a mean grain size of less than 50 micrometers.

The present invention provides a facile and rapid method of production of substantially free flowing powders of micrometer grain size primarily silver sulfate particles with uniform morphology and size produced by aqueous precipitation methods well adapted to large-scale commercial production. The precipitated micron-sized particle grains are stabilized against excessive aggregation by the organo-sulfate or organo-sulfonate additive, resulting in less agglomerated and stable aqueous dispersions and dry or substantially dry powders of silver sulfate. The invention avoids or limits need for any additional and potentially complicating steps of milling, grinding and sieving that may be required to obtain equivalent-sized particle grains of silver sulfate from materials precipitated in the absence of the organo-sulfate or organo-sulfonate additives.

The materials provided by the invention often possess improved thermal stability in the form of reduced discoloration from the direct heating of the materials or heating of composites of the materials of the inventions in combination with plastics, polymers, resins, etc.; and impart antibacterial, antifungal and antiviral properties.

DETAILED DESCRIPTION OF THE INVENTION

In accordance with the process of the present invention, an aqueous solution of a soluble silver salt and an aqueous solution of a source of inorganic sulfate ion may be added together under turbulent mixing conditions in a precipitation reactor. In the absence of the invention, such a precipitation reaction has been found to typically result in substantial agglomeration (aggregation) of the precipitated primary crystallites such that the actual precipitated particle grain sizes may be significantly larger than may be desired for some applications. In accordance with the present invention, it has been found that performing the precipitation of silver sulfate particles in the reactor in the presence of an effective minor amount of an organo-sulfate or organo-sulfonate additive enables obtaining stable, micrometer size (e.g. less than about 50 micrometer) dispersed primarily silver sulfate particles, of a grain size smaller than that obtained in the absence of the organo-sulfate or organo-sulfonate additive.

The terms "organo-sulfate" and "organo-sulfonate" are employed in the present invention to refer to compounds comprising an organic moiety having at least one of either a $-SO_3H$ or $-OSO_3H$ group, or salt thereof, linked to the organic moiety. Preferred organo-sulfate and organo-sulfonate compounds are acidic compounds and alkali metal salts thereof. The additive compound preferably has an aqueous solubility of at least 1 g/L. The organo-sulfate or organo-sulfonate additive compound is added to the precipitation reactor as a minor component (i.e., less than 50 molar percent), relative to the molar amount of silver, effective for obtaining stable, primarily silver sulfate particles of a mean size less than 50 microns. As demonstrated in the examples, effective amounts of additive required may depend upon the specific organo-sulfate or organo-sulfonate additive compound employed, but generally will typically be at least about 0.01 molar percent, based on the molar amount of silver reacted, although even lower concentrations may also be effective depending upon optimized precipitation reaction conditions. By restricting the amount of additive to a minor molar amount relative to the amount of silver, negative attributes associated with the organic character of the additive may be controlled in the resulting precipitated particles comprising primarily silver sulfate, while the minor amounts of additive may still be effective to achieve the desired precipitated particle size. In preferred embodiments of the invention, additives are selected which are effective at molar amounts less than 20 percent, more preferably less than 10 percent, and most preferably less than 5 percent, based on the molar amount of silver.

In general, it has been found that higher molecular weight organo-sulfate or organo-sulfonate additive compounds (e.g., those comprising an organic moiety containing greater than 8 carbon atoms) are more effective than lower molecular weight compounds, and thus require relatively lower molar percentages to be effective. Organo-sulfate and organo-sulfonate additives comprising 8 or less carbon atoms may typically need to be present at somewhat higher molar percentages than higher molecular weight additives to be effective at producing stable precipitated particles of less than 50 micrometer size, such as at least about 0.1 molar percent, or even at least about 1.0 molar percent, based on the molar amount of silver reacted, although even higher concentrations may be required to be effective depending upon optimized precipitation reaction conditions. Organo-sulfate additives comprising even the slightest organic character (i.e., a single carbon atom), however, have been found to be effective in a minor amount relative to the amount of precipitated silver sulfate. Polymeric additives comprising multiple sulfonate groups may be particularly effective at low molar percentages. Thus, in preferred embodiments, the additive compound comprises an alkyl sulfate or alkyl sulfonate compound (each more preferably comprising an alkyl group of more than 8 carbon atoms), or a sulfonated polymeric compound. In most preferred embodiments, the additive employed may be sodium dodecylsulfate or polystyrene sulfonate. In various embodiments of the invention, the organo-sulfate or organo-sulfonate compound may be added to the reactor before, during or after addition of the silver salt solution or sulfate solution to the precipitation reactor.

Soluble silver salts that may be employed in the process of the invention include silver nitrate, acetate, propionate, chlorate, perchlorate, fluoride, lactate, etc. Inorganic sulfate ion sources include sulfuric acid, ammonium sulfate, alkali metal (lithium, sodium, potassium, rubidium, cesium) sulfate, and alkaline earth metal (such as magnesium) sulfate, transition metal (such as zinc, cadmium, zirconium, yttrium, copper, nickel, iron) sulfate, etc. In preferred embodiments of the invention, the soluble silver salt employed is silver nitrate and the source of inorganic sulfate ion is ammonium sulfate or sulfuric acid.

Turbulent mixing conditions employed in precipitation reactors in accordance with the process of the invention may be obtained by means of conventional stirrers and impellers. In a specific embodiment of the invention, the reactants are preferably contacted in a highly agitated zone of a precipitation reactor. Preferred mixing apparatus, which may be used in accordance with such embodiment, includes rotary agitators of the type which have been previously disclosed for use in the photographic silver halide emulsion art for precipitating silver halide particles by reaction of simultaneously introduced silver and halide salt solution feed streams. Such rotary agitators may include, e.g., turbines, marine propellers, discs, and other mixing impellers known in the art (see, e.g., U.S. Pat. No. 3,415,650; U.S. Pat. No. 6,513,965, U.S. Pat. No. 6,422,736; U.S. Pat. No. 5,690,428, U.S. Pat. No. 5,334,359, U.S. Pat. No. 4,289,733; U.S. Pat. No. 5,096,690; U.S. Pat. No. 4,666,669, EP 1156875, WO-0160511).

While the specific configurations of the rotary agitators which may be employed in preferred embodiments of the invention may vary significantly, they preferably will each employ at least one impeller having a surface and a diameter, which impeller is effective in creating a highly agitated zone in the vicinity of the agitator. The term "highly agitated zone" describes a zone in the close proximity of the agitator within which a significant fraction of the power provided for mixing is dissipated by the material flow. Typically, it is contained within a distance of one impeller diameter from a rotary impeller surface. Introduction of a reactant feed stream into a precipitation reactor in close proximity to a rotary mixer, such that the feed stream is introduced into a relatively highly agitated zone created by the action of the rotary agitator provides for accomplishing meso-, micro-, and macro-mixing of the feed stream components to practically useful degrees. Depending on the processing fluid properties and the dynamic time scales of transfer or transformation processes associated with the particular materials employed, the rotary agitator preferably employed may be selected to optimize meso-, micro-, and macro-mixing to varying practically useful degrees.

Mixing apparatus that may be employed in one particular embodiment of the invention includes mixing devices of the type disclosed in Research Disclosure, Vol. 382, February 1996, Item 38213. In such apparatus, means are provided for introducing feed streams from a remote source by conduits that terminate close to an adjacent inlet zone of the mixing device (less than one impeller diameter from the surface of the mixer impeller). To facilitate mixing of multiple feed streams, they may be introduced in opposing direction in the vicinity of the inlet zone of the mixing device. The mixing device is vertically disposed in a reaction vessel, and attached to the end of a shaft driven at high speed by a suitable means, such as a motor. The lower end of the rotating mixing device is spaced up from the bottom of the reaction vessel, but beneath the surface of the fluid contained within the vessel. Baffles, sufficient in number to inhibit horizontal rotation of the contents of the vessel, may be located around the mixing device. Such mixing devices are also schematically depicted in U.S. Pat. Nos. 5,549,879 and 6,048,683; the disclosures of which are incorporated by reference.

Mixing apparatus that may be employed in another embodiment of the invention includes mixers that facilitate separate control of feed stream dispersion (micromixing and mesomixing) and bulk circulation in the precipitation reactor (macromixing), such as descried in U.S. Pat. No. 6,422,736, the disclosure of which is incorporated by reference. Such apparatus comprises a vertically oriented draft tube, a bottom impeller positioned in the draft tube, and a top impeller positioned in the draft tube above the first impeller and spaced there from a distance sufficient for independent operation. The bottom impeller is preferably a flat blade turbine (FBT) and is used to efficiently disperse the feed streams, which are added at the bottom of the draft tube. The top impeller is preferably a pitched blade turbine (PBT) and is used to circulate the bulk fluid through the draft tube in an upward direction providing a narrow circulation time distribution through the reaction zone. Appropriate baffling may be used. The two impellers are placed at a distance such that independent operation is obtained. This independent operation and the simplicity of its geometry are features that make this mixer well suited in the scale-up of precipitation processes. Such apparatus provides intense micromixing, that is, it provides very high power dissipation in the region of feed stream introduction.

Once formed in an aqueous precipitation process in accordance with the invention, the resulting ultra-fine silver sulfate particles may be washed, dried and collected as a white free-flowing powder. In terms of particle size metrics, the precipitation process preferably results in producing both a small primary crystallite size and a small grain size, along with a narrow grain size distribution.

In discussing silver sulfate particle morphology and metrology it is important to clearly understand the definitions of some elementary and widely used terms. By primary crystallite size, one refers to that size which is commonly determined by X-Ray Powder Diffraction (XRPD). A wider XRPD line width implies a smaller primary crystallite size. Quantitatively, the crystallite size (t) is calculated from the measured X-ray peak half width (B (radians)), the wavelength of the X-ray ($\lambda$), and the diffraction angle ($\theta$) using the Scherrer equation:

$$t=0.9\lambda/(B \cos \theta)$$

See B. D. Cullity, "Elements of X-Ray Diffraction" (1956) Addison-Wesley Publishing Company, Inc., Chapter 9.

From a structure view, a crystallite is typically composed of many unit cells, one unit cell being the most irreducible representation of the crystal structure. The primary crystallite size should not be confused with the final grain size. The final grain size is determined by how many of the crystallites agglomerate. Typically, the grain size measurement, including size frequency distribution, can be determined from light scattering measurements provided, for instance, by an LA-920 analyzer available from HORIBA Instruments, Inc. (Irvine, Calif., USA). It is important to make the distinction that having a small primary crystallite size does not guarantee a small final grain size—this must be measured separately from the XRPD spectrum. However, a large primary crystallite size will preclude a small final grain size. Thus to fully characterize a particulate dispersion one would need a knowledge of final grain size (e.g. HORIBA), size-frequency distribution embodied, for example, in the standard deviation (e.g. HORIBA), and primary crystallite size (XRPD).

In preferred embodiments, silver sulfate particles obtained in accordance with the invention can be combined with a thermoplastic, including thermoset, polymers to form a composite, where the composite is defined as the silver sulfate dispersed in the polymer after thermal processing. The preferred thermoplastic polymers suitable for making composites are those polymeric compounds having good thermal stability and a range of melt index, preferably from about 0.3 to about 99. Examples include, but are not limited to, polyolefins such as polyethylene and polypropylene, polystyrene, ABS resins, PVC resins, polyamide including nylon, polyether block amide including PEBAX, polyester, polycarbonate resins, polyvinylpyrolidinone, polyethylene oxide, and the like, as well as their interpolymers and blends, unsaturated polyesters, alkyds, phenolic polymers, amino plastics, epoxy resins, polyurethanes, and polysulfides.

A preferred method for making the composite of the silver sulfate, together with any optional addenda, in polymer is melt blending with the thermoplastic polymer using any suitable mixing device such as a single screw compounder, blender, paddle compounder such as a Brabender, spatula, press, extruder, or molder such as an injection molder. However, it is preferred to use a suitable batch mixer, continuous mixer twin-screw compounder such as a Poly-Lab or Leistritz, to ensure proper mixing and more uniform dispersal. Twin-screw extruders are built on a building block principle. Thus, mixing of silver sulfate, temperature, mixing rotations per minute (rpm), residence time of resin, as well as point of addition of silver sulfate can be easily changed by changing screw design, barrel design and processing parameters. Similar machines are also provided by other twin-screw compounder manufacturers like Werner and Pfleiderrer, Berstorff, and the like, which can be operated either in the co-rotating or the counter-rotating mode.

One method for making the composite is to melt polymer in a glass, metal or other suitable vessel, followed by addition of the silver sulfate salt of this invention. The polymer and silver sulfate are mixed using a spatula until the silver sulfate is uniformly dispersed in the polymer. Another method for making the composite is to melt the polymer in a small compounder, such as a Brabender compounder, followed by addition of the silver sulfate salt of this invention. The polymer and silver sulfate are mixed using the compounder until the silver sulfate is uniformly dispersed in the polymer. Alternatively, the silver sulfate of this invention can be predispersed in the polymer followed by addition of this mixture to the mixing device. Yet, in another method such as in the case of a twin-screw compounder, this compounder is provided with main feeders through which resins are fed, while silver sulfate might be fed using one of the main feeders or using the side stuffers. If the side stuffers are used to feed the silver sulfate then screw design needs to be appropriately configured. The preferred mode of addition of silver sulfate material to the thermoplastic polymer is through the use of the side stuffer, though top feeder can be used, to ensure proper viscous mixing and to ensure dispersion of the silver sulfate through the polymer matrix as well as to control the thermal history. In this mode, the thermoplastic polymer is fed using the main resin feeder, and is followed by the addition of the silver sulfate through the downstream side stuffer. Alternatively, the polymer and silver sulfate can be fed using the main feeders at the same location. In yet another embodiment the silver sulfate can be pre-dispersed in a thermoplastic polymer in a masterbatch, and further diluted in the compounder. As before, the masterbatch and the thermoplastic polymer can be fed through the main resin feeder and/or the side or top feeder, depending on specific objectives. It is preferred that the resultant composite material obtained after compounding is further processed into pellets, granules, strands, ribbons, fibers, powder, films, plaques and the like for subsequent use.

The weight ratio of silver sulfate to thermoplastic polymer in the composite may vary widely depending on application. However, it is preferred that the ratio is $\geq 0.01:99.99$, more preferably $\geq$ about 1:99, and most preferably $\geq$ about 5:95.

Besides the polymer and silver sulfate, the composite material or masterbatch can include any optional addenda. These addenda can include nucleating agents, fillers, plasticizers, surfactants, intercalates, compatibilizers, coupling agents, impact modifiers, chain extenders, colorants, lubricants, antistatic agents, pigments such as titanium oxide, zinc oxide, talc, calcium carbonate, dispersants such as fatty amides (e.g. stearamide), metallic salts of fatty acids (e.g. zinc stearate, magnesium stearate), dyes such as ultramarine blue, cobalt violet, antioxidants, fluorescent whiteners, ultraviolet absorbers, fire retardants, abrasives or roughening agents such as diatomaceous earth, cross-linking agents, foaming agents and the like. These optional addenda and their corresponding amounts can be chosen according to need. Incorporation of these optional addenda in the purge material can be accomplished by any known method.

Silver sulfate particles precipitated in accordance with the invention can be incorporated within plastics and polymers to provide antimicrobial (antibacterial and/or antifungal) or antiviral protection to the plastics and polymers in a variety of end-use applications. Typical end-use applications include, but are not limited to, extruded and non-extruded face fibers for area rugs (rugs with polypropylene face fibers (such as commercial, retail or residential carpet); carpet backing (either primary or secondary backing), or the latex adhesive backings used in carpet (commercial, residential or retail), or area rugs (commercial or residential)). In addition, antimicrobial-incorporated and antiviral-incorporated polymers may also be used in liquid filtration media (such as non-woven filtration media for pools and spas, waste water treatment, potable water treatment, and industrial applications such as metalworking); non-woven air filtration media (such as commercial and residential furnace, HVAC or humidity control filters, air purifiers, and HEPA filters, and cabin air filters for automobiles and airplanes). Further, antimicrobial-incorporated polymers can be used for outdoor fabrics (such as woven and non-woven car and boat covers, tarps, tents, canvas, sails, ropes, pool covers, patio upholstery (such as umbrellas, awnings, seating), camping gear and geotextiles), building materials (such as drywall, weather stripping, insulation, housewrap and roof wrap, wall paper, flooring materials such as cement, concrete, mortar and tile, synthetic marble for kitchen and bath counters and sinks, sanitary ceramics, toilets, shower stalls and curtains, sealing materials (such as adhesives for plumbing and packaging, glazing for windows, tile and vitreous china, grout), push buttons for elevators, handrails for stairs, mats, and knobs), industrial equipment (such as tape, tubing, barrier fabrics, conveyor belts, insulators and insulation for wire and cable, plumbing supplies and fixtures, gaskets, collection and storage equipment (including piping systems, silos, tanks and processing vessels) and coatings used on the inside of fire system sprinkler pipes), daily necessities (such as chopping boards, disposable gloves, bowls, kitchen drain baskets, kitchen refuse baskets, kitchen knife handles, chopsticks, tableware, table cloths, napkins, trays, containers, lunch boxes, chopstick cases, dusters, sponges, brooms, mops, wipes, bathroom stools, washbowls, pales, cupboards, soap cases, shampoo holders, toothbrush holders, toothbrushes, razor blade handles, wrapping films, food wraps and packaging, canteens, emergency water tanks, toilet seats, hairbrushes, combs, scrubbers, tools and tool handles, cosmetics and cosmetic containers, and clothing). Other uses envisioned include incorporation the materials of the invention into stationary and writing materials (such as mechanical pencils, ball-point pens, pencils, erasers, floppy disk cases, clipboards, clear paper holders, fancy cases, video tape cases, photo-magnetic disk shells, compact disk cases, desk mats, binders, book covers, writing paper and pocket books), automobile parts (such as a steering wheels, armrests, panels, shift knobs, switches, keys, door knobs, assist grips), appliances (such as refrigerators, washing machines, vacuum cleaners and bags, air conditioners, clothing irons, humidifiers, dehumidifiers, water cleaners, dish washers and dryers, rice cookers, stationary and mobile telephones, copiers, touch panels for ATM or retail kiosks (e.g. photo-kiosks, etc.)), textile products (such as socks, pantyhose, undergarments, inner liners for jackets, gloves and helmets, towels, bathing suits, toilet covers, curtains, carpet fibers, pillows, sheets, bedclothes, mattress ticking, sleeping bags, nose and mouth masks, towels, caps, hats, wigs, etc.) goods related to public transportation (such as overhead straps, handles and grips, levers, seats, seat belts, luggage and storage racks) sporting goods (such as balls, nets, pucks, whistles, mouth pieces, racket handles, performance clothing, protective gear, helmets, indoor and outdoor artificial turf, shoe linings and reinforcements, tools, structures and ceremonial objects used in athletic events and the martial arts), medical applications (such as bandages, gauze, catheters, artificial limbs, implants, instruments, scrubs, facemasks, shields, reusable and disposable diapers, sanitary napkins, tampons, condoms, uniforms, gowns and other hospital garments requiring aggressive and harsh cleaning treatments to allow the garment to be safely worm by more than one person). Miscellaneous applications for the invention further involve inclusion in musical instruments (such as in reeds, strings and mouthpieces), contact lens, lens keepers and holders, plastic credit/debit cards, sand-like materials for play boxes, cat and pet litter, jewelry and wrist watch bands.

Application of the materials of this invention in polymer-wood composites is also contemplated. With the rising cost of wood and the shortage of mature trees, there is a need to find good quality substitutes for wood that are more durable and longer-lasting (less susceptible to termite destruction and wood rot). Over the past several years, a growing market has emerged for the use of polymer-wood composites to replace traditional solid wood products in end-use applications such as extruded and foam-filled extruded building and construction materials (such as window frames, exterior cladding, exterior siding, door frames, ducting, roof shingles and related roofline products, and exterior boardwalks and walkways); interiors and internal finishes (for example, interior paneling, decorative profiles, office furniture, kitchen cabinets, shelving, worktops, blinds and shutters, skirting boards, and interior railings); automotive (including door and head liners, ducting, interior panels, dashboards, rear shelves, trunk floors, and spare tire covers); garden and outdoor products (such as decking, fence posts and fencing, rails and railings, garden furniture, sheds and shelters, park benches, playground equipment, and playground surfaces); and finally, industrial applications (including industrial flooring, railings, marine pilings, marine bulkheads, fishing nets, railroad ties, pallets, etc.). Polymer-wood composites also offer anti-sapstain protection.

Polymer-wood composites may vary widely in composition, with polymer content typically ranging from about 3-80% by weight depending on end-use. Injection molded products require adequate flow of the molten material; and therefore, preferably contain from about 65 to 80% by weight of the polymer component. Whereas composites requiring structural strength may typically contain only about 3-20% polymer by weight, the polymer typically serving primarily as an adhesive. Perhaps the most commonly employed polymer components are the polyolefins (polyethylene or polypropylene, high density and low density versions and mixtures thereof), although polybutene, polystyrene, and other polymers with melting temperatures between about 130°-200° C. are also used. In principal, any polymer with a melt temperature below the decomposition temperature of the cellulosic fiber component may be employed. Crosslinking chemicals (such as peroxides and vinylsilanes), compatibilizers and coupling agents (such as grafted-maleic anhydride polymers or copolymers) that incorporate functionality capable of forming covalent bonds within or between the polymer and cellulosic components may be included. Cellulosic materials can be obtained from a wide variety of sources: wood and wood products, such as wood pulp fibers; non-woody paper-making fibers from cotton; straws and grasses, such as rice and esparto; canes and reeds, such as bagasse; bamboos; stalks with bast fibers, such as jute, flax, kenaf, linen and ramie; and leaf fibers, such as abaca and sisal; paper or polymer-coated paper including recycled paper and polymer-coated paper. One or more cellulosic materials can be used. More commonly, the cellulosic material used is from a wood source. Suitable wood sources include softwood sources such as pines, spruces, and firs, and hardwood sources such as oaks, maples, eucalyptuses, poplars, beeches, and aspens. The form of the cellulosic materials from wood sources can be sawdust, wood chips, wood flour, or the like. Still, microbes such as bacteria and fungus can feed on plasticizers or other additives and environmental foodstuffs found in or on the polymer component, resulting in discoloration and structural (chemical or mechanical) degradation. The present invention provides a means to more effectively address these issues by incorporating antimicrobial or antiviral agents in either or both of the polymer and wood components of these composites.

Another emerging application to which the present invention is particularly applicable is antimicrobial nonwoven fabrics. In general, continuous filament nonwoven fabric formation involves supplying a low viscosity molten polymer that is then extruded under pressure through a large number of micro-orifices in a plate known as a spinneret or die, which creates a plurality of continuous polymeric filaments. The filaments are then quenched and drawn, and collected to form a nonwoven web. Extrusion of melt polymers through micro-orifices requires that polymer additives have particle sizes significantly smaller than the orifice diameter. It is preferred that the additive particles be less than a quarter of the diameter of the orifice holes to avoid process instabilities such as filament breakage and entanglement, or "roping", of filaments while still in the molten state. Microfilaments may typically be on the order of about 20 microns in diameter, while super microfilaments may be on the order of 3-5 microns. Continuous filament nonwoven fabrics formed from super microfilaments are mainly used in air filters, as well as in artificial leathers and wipes. Commercial processes are well known in the art for producing continuous microfilament nonwoven fabrics of polyethylene and polypropylene. As demonstrated in the examples below, the present invention enables production of stable silver sulfate particles having mean sizes of less than 20 micrometers, and even less than 5 micrometers, and accordingly may be optimized to meet the stringent size requirements for particles to be incorporated into such fine filaments.

EXAMPLES

The invention is further illustrated by the following examples.

Examples 1-21

Precipitation of Silver Sulfate Particles

In Examples 1-21, thermal discoloration analysis was performed by heating 1-2 g of air-dried samples of indicated material in a small petri dish (5.5 cm diameter) in a Barnstead International 48000 Furnace. Typically, samples were heated from 125° C. to 260° C. holding for 10' at 125, 175, 230 and 260° C. Some samples that showed minimal discoloration at 260° C. were heated to 300° C. and higher. Samples were removed from the furnace as soon as they showed noticeable discoloration. Characterization of sample discoloration was made visually.

Example 1

Comparative, No Additive, Sulfuric Acid

A six-liter stainless steel sponge kettle was charged with 2 L of distilled water and the temperature controlled at 10° C. A planar mixing device previously described (Research Disclosure 38213, February 1996 pp 111-114 "Mixer for Improved Control Over Reaction Environment") operating at 3000 rpm was used to ensure the homogeneity of the reactor contents. To this reactor 180 mL of a 8M solution of $H_2SO_4$ was added. The resultant pH was <1. A peristaltic pump was used to deliver a 639 mL solution containing 3M silver nitrate at a rate of 225 mL/min causing precipitation of a white product after ~20 s. The measured pH was ~1. The reaction was held at 10° C. for 10 min. The final product was washed to a conductivity of <10 mS and a portion was dried at ambient temperature. Powder X-ray diffraction confirmed the product was single-phase silver sulfate. The mean grain size was determined by light scattering (HORIBA) to be 59 μm with a standard deviation of 29 μm. Optical micrographs of dried product indicated a mean grain size consistent with that found from the light scattering measurement. Thermal discoloration analysis of dried product showed that it remained white up to 450° C. (highest temperature tested).

Example 2

Comparative, No Additive, Sodium Sulfate

A six-liter stainless steel sponge kettle was charged with 2 L of distilled water and the temperature controlled at 10° C. The reactor contents were mixed as described in Example 1. To this reactor 780 g of $Na_2SO_4 \cdot 10H_2O$ (Aldrich, 99+%) were added and dissolved. The resultant pH was 6.6. A peristaltic pump was used to deliver a 1278 mL solution containing 3M silver nitrate at a rate of 225 mL/min causing precipitation of a white product after ~25 s. The measured pH was 4.2. The reaction was held at 10° C. for 10 min. The final product was washed to a conductivity of <10 mS and a portion was dried at ambient temperature. The mean grain size was determined to be 62 μm by light scattering (HORIBA). Thermal discoloration analysis of dried product showed that it started to turn from white to yellow after ~5 min at 230° C.

Example 3

Comparative, No Additive, Ammonium Sulfate

A six-liter stainless steel kettle was charged with 2 L of distilled water and the temperature controlled at 10° C. The reactor contents were mixed as described in Example 1. To this reactor 159.9 g of $(NH_4)_2SO_4$ (Aldrich, 99+%) were added and dissolved. The resultant pH was 5.5. A peristaltic pump was used to deliver a 639 mL solution containing 3M silver nitrate at a rate of 225 mL/min causing precipitation of a white product. The measured pH was 4.1. The reaction was held at 10° C. for 10 min. The final product was washed to a conductivity of <10 mS and a portion was dried at ambient temperature. The mean grain size was determined to be 54 μm by light scattering (HORIBA). Thermal discoloration analysis of dried product showed that it started to turn from white to off-white after ~5 min at 230° C.

Example 5

Comparative, Tridecyl Phosphate Additive

A six-liter stainless steel sponge kettle was charged with 2 L of distilled water and the temperature controlled at 10° C. The reactor contents were mixed as described in Example 1. To this reactor 426 mL of a solution containing 130 g of $Na_2SO_4 \cdot 10H_2O$ and 50 mL of a solution containing 0.5 g tridecyl phosphate were added. The resultant pH was 4.2. The pH was adjusted to 6.8 with $NH_4OH$. A peristaltic pump was used to deliver a 213 mL solution containing 3M silver nitrate at a rate of 225 mL/min causing precipitation of a white product. The measured pH was 4.3. The reaction was held at 10° C. for 10 min. The final product was washed to a conductivity of <10 mS. The mean grain size was determined to be 67 μm by light scattering (HORIBA). Thermal discoloration analysis of dried product showed that it started to turn from white to light yellow after ~5 min at 230° C.

Example 6

Comparative, Aquazol 50 (poly(2-ethyl-2-oxazoline) Additive

A six-liter stainless steel sponge kettle was charged with 2 L of distilled water and the temperature controlled at 10° C. The reactor contents were mixed as described in Example 1. To this reactor 180 mL of a 8M solution of $H_2SO_4$ was added. The resultant pH was <1. Subsequently, a 28-30% solution of $NH_4OH$ was added until the pH reached 7 (effectively making $(NH_4)_2SO_4$ in situ). A 200 mL solution containing 2 g of Aquazol 50 ((poly (2-ethyl-2-oxazoline), MW 50,000) was then added to the kettle resulting in a pH of 7.2. A peristaltic pump was used to deliver a 639 mL solution containing 3M silver nitrate at a rate of 225 mL/min causing precipitation of a white product. The measured pH was 4.7. The reaction was held at 10° C. for 10 min. The final product was washed to a conductivity of <10 mS and a portion was dried at ambient temperature. The mean grain size was determined to be 75 μm by light scattering (HORIBA). Thermal discoloration analysis of dried product showed that it remained white up to 260° C. (highest temperature tested).

Example 7

Comparative, Polyvinylpyrrolidone Additive

A six-liter stainless steel sponge kettle was charged with 2 L of distilled water and the temperature controlled at 10° C. The reactor contents were mixed as described in Example 1. To this reactor 180 mL of a 8M solution of $H_2SO_4$ was added. The resultant pH was <1. Subsequently, a 28-30% solution of $NH_4OH$ was added until the pH reached 7 (effectively making $(NH_4)_2SO_4$ in situ). A 200 mL solution containing 2 g of polyvinylpyrrolidone (MW 10,000) was then added to the kettle resulting in a pH of 7.1. A peristaltic pump was used to deliver a 639 mL solution containing 3M silver nitrate at a rate of 225 mL/min causing precipitation of a white product. The measured pH was 4.6. The reaction was held at 10° C. for 10 min. The final product was washed to a conductivity of <10 mS and a portion was dried at ambient temperature. The mean grain size was determined to be 57 μm by light scattering (HORIBA). Thermal discoloration analysis of dried product showed that it started to turn from white to tan after ~5 min at 175° C.

Example 8A

Comparative, Sodium Methyl Sulfate Additive (Ineffective)

A six-liter stainless steel kettle was charged with 2 L of distilled water and the temperature controlled at 10° C. The reactor contents were mixed as described in Example 1. To this reactor 180 mL of a 8M solution of $H_2SO_4$ and 2 g of sodium methyl sulfate were added. The resultant pH was <1. A peristaltic pump was used to deliver a 639 mL solution containing 3M silver nitrate at a rate of 225 mL/min causing precipitation of a white product. The measured pH was ~1. The reaction was held at 10° C. for 10 min. The final product was washed to a conductivity of <10 mS and a portion was dried at ambient temperature. The mean grain size for comparative Example 8A was determined to be 63 μm by light scattering (HORIBA). Thermal discoloration analysis of dried product showed that it remained white up to 260° C. (highest temperature tested).

Example 8B

Inventive, Sodium Methyl Sulfate Additive (Effective)

The reaction of Example 8A was repeated with modification, employing ammonium sulfate in place of sulfuric acid, and a higher level of additive. A six-liter stainless steel sponge kettle was charged with 2 L of distilled water and the temperature controlled at 10° C. The reactor contents were mixed as described in Example 1. To this reactor 640 mL of a solution containing 190.1 g of $(NH_4)_2SO_4$ and 10 g of sodium methyl sulfate were added. The resultant pH was 6.4. A peristaltic pump was used to deliver a 640 mL solution containing 3.1M silver nitrate at a rate of 225 mL/min causing precipitation of a white product. The measured pH was 4.4. The reaction was held at 10° C. for 10 min. The final product was washed to a conductivity of <10 mS. The mean grain size of inventive Example 8B was determined to be 45 μm by light scattering (HORIBA).

Example 9

Comparative, 2-aminoethyl Hydrogensulfate Additive

A six-liter stainless steel kettle was charged with 2 L of distilled water and the temperature controlled at 10° C. The reactor contents were mixed as described in Example 1. To this reactor 180 mL of a 8M solution of $H_2SO_4$ and 2 g of 2-aminoethylhydrogensulfate were added. The resultant pH was <1. A peristaltic pump was used to deliver a 639 mL solution containing 3M silver nitrate at a rate of 225 mL/min causing precipitation of a white product. The measured pH was ~1. The reaction was held at 10° C. for 10 min. The final product was washed to a conductivity of <10 mS and a portion was dried at ambient temperature. The mean grain size was determined to be 65 μm by light scattering (HORIBA). Thermal discoloration analysis of dried product showed that it remained white up to 260° C. (highest temperature tested).

Example 10

Comparative, Cyclohexylsulfamic Acid Additive

A six-liter stainless steel kettle was charged with 2 L of distilled water and the temperature controlled at 10° C. The reactor contents were mixed as described in Example 1. To this reactor 180 mL of a 8M solution of $H_2SO_4$ and 2 g of cyclohexylsulfamic acid were added. The resultant pH was <1. A peristaltic pump was used to deliver a 639 mL solution containing 3M silver nitrate at a rate of 225 mL/min causing precipitation of a white product. The measured pH was ~1. The reaction was held at 10° C. for 10 min. The final product was washed to a conductivity of <10 mS and a portion was dried at ambient temperature. The mean grain size was determined to be 63 μm by light scattering (HORIBA). Thermal discoloration analysis of dried product showed that it remained white up to 260° C. (highest temperature tested).

Example 11A

Comp, Sodium 2-ethylhexylsulfate (Stepanol EHS) (Ineffective)

A six-liter stainless steel kettle was charged with 2 L of distilled water and the temperature controlled at 10° C. The reactor contents were mixed as described in Example 1. To this reactor 180 mL of a 8M solution of $H_2SO_4$ and 5 g of a solution (Stepan Stepanol EHS) containing 2 g of sodium 2-ethyl hexyl sulfate were added. The resultant pH was <1. A peristaltic pump was used to deliver a 639 mL solution containing 3M silver nitrate at a rate of 225 mL/min causing precipitation of a white product. The measured pH was 1. The reaction was held at 10° C. for 10 min. The final product was washed to a conductivity of <10 mS and a portion was dried at ambient temperature. The mean grain size was determined to be 65 μm by light scattering (HORIBA). The dried powder was off-white and thermal discoloration analysis showed that comparative Example 11A remained this color up to 260° C. (highest temperature tested).

Example 11B

Inventive, Sodium 2-ethylhexylsulfate (Stepanol EHS) (Effective)

The previous reaction of Example 11A was repeated with modifications. After the addition of $H_2SO_4$ resulted in a pH of <1, a 28-30% solution of $NH_4OH$ was subsequently added until the pH reached 7 (effectively making $(NH_4)_2SO_4$ in situ). A 200 mL solution containing 5 g of a solution (Stepan Stepanol EHS) containing 2 g of sodium 2-ethylhexylsulfate was added to the kettle resulting in a pH of 7.2. A peristaltic pump was used to deliver a 639 mL solution containing 3M silver nitrate at a rate of 225 mL/min causing precipitation of a white product. The measured pH was 5.0. The reaction was held at 10° C. for 10 min. The final product was washed to a conductivity of <10 mS and a portion was dried at ambient temperature. The mean grain size of inventive Example 11B was determined to be 43 μm by light scattering (HORIBA). Thermal discoloration analysis of dried product showed that it started to turn from white to yellow after ~5 min at 230° C.

Example 11C

Inventive, Sodium 2-ethylhexylsulfate (Stepanol EHS) (Effective)

The previous reaction of Example 11A was repeated with further modifications, employing ammonium sulfate in place of sulfuric acid, and a higher level of additive. A six-liter stainless steel sponge kettle was charged with 2 L of distilled water and the temperature controlled at 10° C. The reactor contents were mixed as described in Example 1. To this reactor 640 mL of a solution containing 190.1 g of $(NH_4)_2SO_4$ and 100 g of a solution (Stepan Stepanol EHS) containing 40 g of sodium 2-ethylhexylsulfate were added. Addition of the sodium 2-ethyl hexyl sulfate solution noticeably thickened the reactor solution and resulted in some foam formation. The resultant pH was 7.0. A peristaltic pump was used to deliver a 640 mL solution containing 3.1M silver nitrate at a rate of 225 mL/min causing precipitation of a white product. The measured pH was 4.9. The reaction was held at 10° C. for 10 min. The final product was washed to a conductivity of <10 mS. The mean grain size of inventive Example 11C was determined to be 46 μm by light scattering (HORIBA).

Example 12

Comparative, 5-sulfoisophthalic Acid, Sodium Salt

A six-liter stainless steel kettle was charged with 2 L of distilled water and the temperature controlled at 10° C. The reactor contents were mixed as described in Example 1. To this reactor 180 mL of a 8M solution of $H_2SO_4$ was added. The resultant pH was <1. Subsequently, a 28-30% solution of $NH_4OH$ was added until the pH reached 7 (effectively making $(NH_4)_2SO_4$ in situ). This was followed by addition of 2 g of 5-sulfoisophthalic acid (sodium salt), which upon dissolution resulted in a pH of 3.9. The pH was readjusted to 7 with $NH_4OH$. A peristaltic pump was used to deliver a 639 mL solution containing 3M silver nitrate at a rate of 225 mL/min causing precipitation of a white product after 30 s. The measured pH was 4.8. The reaction was held at 10° C. for 10 min. The final product was washed to a conductivity of <10 mS and a portion was dried at ambient temperature. The mean grain size was determined to be 61 μm by light scattering (HORIBA). Thermal discoloration analysis of dried product showed that it started to turn from white to yellow after ~5 min at 260° C.

Example 13A

Comparison, Sodium Octylsulfate (Polystep B-29) (Ineffective)

A six-liter stainless steel kettle was charged with 2 L of distilled water and the temperature controlled at 10° C. The reactor contents were mixed as described in Example 1. To this reactor 426 mL of a solution containing 130 g of $Na_2SO_4 \cdot 10H_2O$ and 3.3 g of a solution (Stepan Polystep B-29) containing 1 g of sodium octyl sulfate were added. The resultant pH was 6.6. A peristaltic pump was used to deliver a 213 mL solution containing 3M silver nitrate at a rate of 225 mL/min causing precipitation of a white product. The measured pH was 5.0. The reaction was held at 10° C. for 10 min. The final product was washed to a conductivity of <10 mS. The mean grain size of comparative Example 13A was determined to be 63 μm by light scattering (HORIBA). Thermal discoloration analysis of dried product showed that it turned from white to yellow after ~5 min at 175° C.

Example 13B

Inventive, Sodium Octylsulfate (Polystep B-29) (Effective)

The previous reaction of Example 13A was repeated with modification, employing ammonium sulfate in place of sodium sulfate, and a higher level of additive. A six-liter stainless steel sponge kettle was charged with 2 L of distilled water and the temperature controlled at 10° C. The reactor contents were mixed as described in Example 1. To this reactor 640 mL of a solution containing 190.1 g of $(NH_4)_2SO_4$ and 40 g of a solution (Stepan Polystep B-29) containing 12 g of sodium octyl sulfate were added. The resultant pH was 5.7. A peristaltic pump was used to deliver a 640 mL solution containing 3.1M silver nitrate at a rate of 225 mL/min causing precipitation of a white product. The measured pH was 4.3. The reaction was held at 10° C. for 10 min. The final product was washed to a conductivity of <10 mS. The mean grain size of inventive Example 13B was determined to be 12 μm by light scattering (HORIBA).

Example 13C

Inventive, Sodium Octylsulfate (Polystep B-29) (Effective)

The previous reaction of Example 13A was repeated with modification, employing ammonium sulfate in place of sodium sulfate, and a higher level of additive. A six-liter stainless kettle was charged with 2 L of distilled water and the temperature controlled at 10° C. The reactor contents were mixed as described in Example 1. To this reactor 640 mL of a solution containing 190.1 g of $(NH_4)_2SO_4$ and 120 g of a solution (Stepan Polystep B-29) containing 36 g of sodium octyl sulfate were added. Addition of the octyl sulfate solution noticeably thickened the reactor solution and resulted in some foam formation. The resultant pH was 6.5. A peristaltic pump was used to deliver a 640 mL solution containing 3.1M silver nitrate at a rate of 225 mL/min causing precipitation of a white product. The measured pH was 4.4. The reaction was held at 10° C. for 10 min. The final product was washed to a conductivity of <10 mS. The mean grain size of inventive Example 13C was determined to be 22 μm by light scattering (HORIBA).

Example 14A

Comparative, 4-vinylbenzene Sulfonic Acid, Sodium Salt (Ineffective)

A six-liter stainless steel kettle was charged with 2 L of distilled water and the temperature controlled at 10° C. The reactor contents were mixed as described in Example 1. To this reactor 180 mL of a 8M solution of $H_2SO_4$ and 2 g of 4-vinylbenzene sulfonic acid (sodium salt) were added. The resultant pH was <1. A peristaltic pump was used to deliver a 639 mL solution containing 3M silver nitrate at a rate of 225 mL/min causing precipitation of a white product. The measured pH was ~1. The reaction was held at 10° C. for 10 min. The final product was washed to a conductivity of <10 mS and a portion was dried at ambient temperature. The mean grain size of comparative Example 14A was determined to be 54 μm by light scattering (HORIBA). Thermal discoloration analysis of dried product showed that it remained white up to 260° C. (highest temperature tested).

Example 14B

Comparison, 4-vinylbenzene Sulfonic Acid (Ineffective)

The previous reaction of Example 14A was repeated with modification. A six-liter stainless steel sponge kettle was charged with 2 L of distilled water and the temperature controlled at 10° C. The reactor contents were mixed as described in Example 1. To this reactor 180 mL of a 8M solution of $H_2SO_4$ was added. The resultant pH was <1. Subsequently, a 28-30% solution of $NH_4OH$ was added until the pH reached 7 (effectively making $(NH_4)_2SO_4$ in situ). A 200 mL solution containing 2 g of 4-vinylbenzene sulfonic acid was added to the kettle resulting in a pH of 7.1. A peristaltic pump was used to deliver a 639 mL solution containing 3M silver nitrate at a rate of 225 mL/min causing precipitation of a white product. The measured pH was 4.9. The reaction was held at 10° C. for 10 min. The final product was washed to a conductivity of <10 mS and a portion was dried at ambient temperature. The mean grain size of inventive Example 14B was determined to be 58 μm by light scattering (HORIBA). Thermal discoloration analysis of dried product showed that it remained white up to 260° C. (highest temperature tested).

Example 15A

Comparison, Sodium Decyl Sulfate (Ineffective)

A six-liter stainless steel sponge kettle was charged with 2 L of distilled water and the temperature controlled at 10° C. The reactor contents were mixed as described in Example 1. To this reactor 640 mL of a solution containing 190.1 g of $(NH_4)_2SO_4$ and 4 g of sodium decyl sulfate were added. The resultant pH was 5.8. A peristaltic pump was used to deliver a 640 mL solution containing 3.1M silver nitrate at a rate of 225 mL/min causing precipitation of a white product. The measured pH was 4.3. The reaction was held at 10° C. for 10 min. The final product was washed to a conductivity of <10 mS. The mean grain size of comparative Example 15A was determined to be 62 μm by light scattering (HORIBA).

Example 15B

Inventive, Sodium Decyl Sulfate (Effective)

The previous reaction of Example 15A was repeated with modification, employing a higher level of additive. A six-liter stainless steel sponge kettle was charged with 2 L of distilled water and the temperature controlled at 10° C. The reactor contents were mixed as described in Example 1. To this reactor 640 mL of a solution containing 190.1 g of $(NH_4)_2SO_4$ and 20 g of sodium decyl sulfate were added. The resultant pH was 6.2. A peristaltic pump was used to deliver a 640 mL solution containing 3.1M silver nitrate at a rate of 225 mL/min causing precipitation of a white product. The measured pH was 4.3. The reaction was held at 10° C. for 10 min. The final product was washed to a conductivity of <10 mS. The mean grain size of inventive Example 15B was determined to be 3 μm by light scattering (HORIBA).

Example 16A

Inventive, Sodium Dodecyl Sulfate

A six-liter stainless steel kettle was charged with 2 L of distilled water and the temperature controlled at 10° C. The reactor contents were mixed as described in Example 1. To this reactor 180 mL of a 8M solution of $H_2SO_4$ and 2 g of sodium dodecyl sulfate (SDS) were added. The resultant pH was <1. A peristaltic pump was used to deliver a 639 mL solution containing 3M silver nitrate at a rate of 225 mL/min causing precipitation of a white product after ~20 s. The measured pH was ~1. The reaction was held at 10° C. for 10 min. The final product was washed to a conductivity of <10 mS and a portion was dried at ambient temperature. Powder X-ray diffraction confirmed the product was single phase silver sulfate. The mean grain size of inventive Example 16A was determined by light scattering (HORIBA) to be 23 μm. Infrared spectrographic analysis of the dried product revealed strong absorption bands at 2920 cm$^{-1}$, 2850 cm$^{-1}$ and 1467 cm$^{-1}$, indicative of retained SDS. Thermal discoloration analysis of dried product showed that it started to turn from white to light gray after ~5 min at 260° C.

Example 16B

Inventive, Sodium Dodecyl Sulfate

The previous reaction of Example 16A was repeated with modification, employing a higher level of additive (increase in the SDS level to 4 g). A mean grain size of 14 μm grain size with a standard deviation of 6 μm was determined by light scattering (HORIBA) for inventive Example 16B. Optical micrographs of dried product indicated a mean grain size less than or equal to 14 microns. Similar results were also obtained when an equimolar amount of $(NH_4)_2SO_4$ was used in place of $H_2SO_4$.

Example 17

Inventive, Sodium Lauryl Ether Sulfate (Polystep B-19)

A six-liter stainless steel kettle was charged with 2 L of distilled water and the temperature controlled at 10° C. The reactor contents were mixed as described in Example 1. To this reactor 426 mL of a solution containing 130 g of $Na_2SO_4.10H_2O$ and 3.3 g of a solution (Stepan Polystep B-19) containing 1 g of sodium lauryl ether sulfate were added. The resultant pH was 6.3. A peristaltic pump was used to deliver a 213 mL solution containing 3M silver nitrate at a rate of 225 mL/min causing precipitation of a white product. The measured pH was 4.8. The reaction was held at 10° C. for 10 min. The final product was washed to a conductivity of <10 mS. The mean grain size was determined to be 33 μm by light scattering (HORIBA). Thermal discoloration analysis of dried product showed that it started to turn from white to tan after ~5 min at 175° C.

Example 18

Inventive, Sodium Nonylphenol Ethoxylate Sulfate (Polystep B-27)

A six-liter stainless steel kettle was charged with 2 L of distilled water and the temperature controlled at 10° C. The reactor contents were mixed as described in Example 1. To this reactor 426 mL of a solution containing 130 g of $Na_2SO_4.10H_2O$ and 3.3 g of a solution (Stepan Polystep B-27) containing 1 g of sodium nonylphenol ethoxylate sulfate were added. The resultant pH was 6.7. A peristaltic pump was used to deliver a 213 mL solution containing 3M silver nitrate at a rate of 225 mL/min causing precipitation of a white product. The measured pH was 5.2. The reaction was held at 10° C. for 10 min. The final product was washed to a conductivity of <10 mS. The mean grain size was determined to be 32 μm by light scattering (HORIBA). Thermal discoloration analysis of dried product showed that it turned from white to dark yellow after ~5 min at 230° C.

Example 19A

Inventive, Sodium Dodecylbenzenesulfonate

A six-liter stainless steel kettle was charged with 2 L of distilled water and the temperature controlled at 10° C. The reactor contents were mixed as described in Example 1. To this reactor 180 mL of a 8M solution of $H_2SO_4$ and 4 g of sodium dodecylbenzenesulfonate were added. The resultant pH was <1. A peristaltic pump was used to deliver a 639 mL solution containing 3M silver nitrate at a rate of 225 mL/min causing precipitation of a white product. The measured pH was ~1. The reaction was held at 10° C. for 10 min. The final product was washed to a conductivity of <10 mS and a portion was dried at ambient temperature. The mean grain size was determined to be 11 µm by light scattering (HORIBA). Thermal discoloration analysis of dried product showed that it started to turn from white to yellow after ~5 min at 230° C.

Example 19B

Inventive, Sodium Dodecylbenzenesulfonate

The previous reaction of Example 19A was repeated with modification, employing a lower level of additive (reducing the sodium dodecylbenzenesulfonate level to 2 g). The resulting mean grain size was determined to be 19 µm by light scattering (HORIBA).

Example 20

Inventive, Sodium bis(2-ethylhexyl) Sulfosuccinate (Aerosol OT)

A six-liter stainless steel kettle was charged with 2 L of distilled water and the temperature controlled at 10° C. The reactor contents were mixed as described in Example 1. To this reactor 426 mL of a solution containing 130 g of $Na_2SO_4 \cdot 10H_2O$ and 80 mL of a solution containing 4 g of sodium bis(2-ethylhexyl) sulfosuccinate were added. The resultant pH was 6.0. A peristaltic pump was used to deliver a 213 mL solution containing 3M silver nitrate at a rate of 225 mL/min causing precipitation of a white product. The measured pH was 4.8. The reaction was held at 10° C. for 10 min. The final product was washed to a conductivity of <10 mS. The mean grain size was determined to be 21 µm by light scattering (HORIBA). Thermal discoloration analysis of dried product showed that it started to turn from white to tan after ~5 min at 175° C.

Example 21

Inventive, Polystyrenesulfonic Acid, Sodium Salt

A six-liter stainless steel kettle was charged with 2 L of distilled water and the temperature controlled at 10° C. The reactor contents were mixed as described in Example 1. To this reactor 180 mL of a 8M solution of $H_2SO_4$ was added. The resultant pH was <1. Subsequently, a 28-30% solution of $NH_4OH$ was added until the pH reached 7 (effectively making $(NH_4)_2SO_4$ in situ). A 200 mL solution containing 2 g of polystyrenesulfonic acid (sodium salt, MW 70,000) was then added to the kettle resulting in a pH of 7.0. A peristaltic pump was used to deliver a 639 mL solution containing 3M silver nitrate at a rate of 225 mL/min causing precipitation of a white product after ~20 s. The measured pH was 4.7. The reaction was held at 10° C. for 10 min. The final product was washed to a conductivity of <10 mS and a portion was dried at ambient temperature. The mean grain size was determined by light scattering (HORIBA) to be 19 µm with a standard deviation of 10.6 µm. Optical micrographs of dried product indicated a mean grain size less than or equal to 19 microns. Infrared spectrographic analysis of the dried product revealed strong absorption bands at 1125 $cm^{-1}$ and 1177 $cm^{-1}$, indicative of retained polystyrenesulfonic acid. Thermal discoloration analysis of dried product showed that it started to turn from white to light brown after ~5 min at 300° C.

The above reaction was repeated using a marine propeller as the mixing device, and product with a similar mean grain size was obtained.

X-ray powder diffraction analysis confirmed the identity of the example materials and the commercially obtained samples as comprising primarily silver sulfate using the Powder Diffraction File reference PDF27-1403 (International Centre for Diffraction Data, 12 Campus Boulevard, Newtown Square, Pa., USA). X-ray peak half widths were all narrow and no distinction could be drawn about crystallite size among the samples other than that, based on the Scherrer equation, the crystallite size was greater than about 100 nanometers in all samples that were examined.

Particle size and thermal stability results for the silver sulfate materials precipitated in Examples 1-21 are summarized in Table 1 below. The amount of the additive is expressed as a molar percent relative to the moles of silver added to the reactor.

TABLE 1

| Ex. | Sulfate source | Additive | Additive mol % | HORIBA (um) | Color | Temp (C.) | Ex. type |
|---|---|---|---|---|---|---|---|
| 1 | sulfuric acid | None | — | 59 | white | 450* | comp. |
| 2 | sodium sulfate | None | — | 62 | yellow | 230 | comp. |
| 3 | ammonium sulfate | None | — | 54 | Off-white | 230 | comp. |
| 4 | sulfuric acid (pH adjust to 7) | None | — | 60 | white | 260* | comp. |
| 5 | sodium sulfate | tridecyl phosphate | 0.56 | 67 | yellow | 230 | comp. |
| 6 | sulfuric acid (pH adjust to 7) | Aquazol 50 (poly (2-ethyl-2-oxazoline) MW 50,000 | 2.06 | 75 | white | 260* | comp. |
| 7 | sulfuric acid (pH adjust to 7) | Polyvinylpyrrolidone MW 10,000 | 1.90 | 57 | Tan | 175 | comp. |
| 8A | sulfuric acid | sodium methyl sulfate | 1.49 | 63 | white | 260* | comp. |

TABLE 1-continued

| Ex. | Sulfate source | Additive | Additive mol % | HORIBA (um) | Color | Temp (C.) | Ex. type |
|---|---|---|---|---|---|---|---|
| 8B | ammonium sulfate | sodium methyl sulfate | 7.41 | 45 | — | — | inv. |
| 9 | sulfuric acid | 2-aminoethyl hydrogensulfate | 1.42 | 65 | white | 260* | comp. |
| 10 | sulfuric acid | cyclohexylsulfamic acid | 1.12 | 63 | white | 260* | comp. |
| 11A | sulfuric acid | sodium 2-ethyl hexyl sulfate (Stepanol EHS) | 0.86 | 65 | white | 260* | comp. |
| 11B | sulfuric acid (pH adjust to 7) | sodium 2-ethyl hexyl sulfate (Stepanol EHS) | 0.86 | 43 | yellow | 230 | inv. |
| 11C | ammonium sulfate | sodium 2-ethyl hexyl sulfate (Stepanol EHS) | 17.2 | 46 | — | — | inv. |
| 12 | sulfuric acid (pH adjust to 7) | 5-sulfoisophthalic acid, sodium salt | 0.75 | 61 | yellow | 260 | comp. |
| 13A | sodium sulfate | sodium octyl sulfate (Polystep B-29) | 0.43 | 63 | yellow | 175 | comp. |
| 13B | ammonium sulfate | sodium octyl sulfate (Polystep B-29) | 5.17 | 12 | — | — | inv. |
| 13C | ammonium sulfate | sodium octyl sulfate (Polystep B-29) | 15.5 | 22 | — | — | inv. |
| 14A | sulfuric acid | 4-vinylbenzene sulfonic acid, sodium salt | 0.97 | 54 | white | 260* | comp. |
| 14B | sulfuric acid (pH adjust to 7) | 4-vinylbenzene sulfonic acid | 0.97 | 58 | white | 260* | comp. |
| 15A | ammonium sulfate | sodium decyl sulfate | 1.69 | 62 | — | — | comp. |
| 15B | ammonium sulfate | sodium decyl sulfate | 8.47 | 3 | — | — | inv. |
| 16A | sulfuric acid | sodium dodecyl sulfate | 0.69 | 23 | light gray | 260 | inv. |
| 16B | sulfuric acid | sodium dodecyl sulfate | 1.39 | 14 | light gray | 260 | inv. |
| 17 | sodium sulfate | sodium lauryl ether sulfate (Polystep B-19) | 0.06 | 33 | Tan | 175 | inv. |
| 18 | sodium sulfate | sodium nonylphenol ethoxylate sulfate (Polystep B-27) | 0.20 | 32 | dark yellow | 230 | inv. |
| 19A | sulfuric acid | Sodium dodecylbenzenesulfonate | 1.15 | 11 | yellow | 230 | inv. |
| 19B | sulfuric acid | Sodium dodecylbenzenesulfonate | 0.57 | 19 | yellow | 230 | inv. |
| 20 | sodium sulfate | sodium bis(2-ethylhexyl) sulfosuccinate (aerosol OT) | 0.90 | 21 | Tan | 175 | inv. |
| 21 | sulfuric acid (pH adjust to 7) | polystyrenesulfonic acid, sodium salt MW 70,000 | 0.97 | 19 | light brown | 300 | inv. |

*Highest temperature tested

Comparison of results above for Examples 1-4, in which no additive was used, indicates that while the source of sulfate ion has a relatively small impact on the grain size of silver sulfate formed (54-62 μM), a more substantial difference is seen in thermal stability. Sulfuric acid and the process of adjusting sulfuric acid to a neutral pH with ammonia gave the least discolored products, ammonium sulfate yielded slightly off-white material, and sodium sulfate produced the greatest discoloration. Comparison of Examples 5-7 to the comparison group of Examples 1-4 indicates that the anionic surfactant tridecyl phosphate and the non-ionic polymeric surfactants poly (2-ethyl-2-oxazoline) and polyvinylpyrrolidone fail to reduce the grain size significantly nor improve thermal instability. In contrast, Examples 8-21 demonstrate that organo-sulfate or organo-sulfonate additives may be employed in amounts effective to exhibit substantially reduced grain sizes. We note that the lower molecular weight organo-sulfate or organo-sulfonate additives of Examples 8-15 may need to be employed at generally higher levels, relative to the higher molecular weight additives of examples 16-21, in order to reduce the grain size to a comparable extent. More specifically, the higher molecular weight organo-sulfate or organo-sulfonate additives of Examples 16-21 typically require less than about 2% on a molar basis relative to silver to reduce the grain size substantially below 50 micrometers, whereas the lower molecular weight additives of the invention often require greater than 5% (e.g. Examples 8B, 13B, 15B) or greater than 15% (e.g. Examples 11C and 13C). While higher levels of relatively low-molecular weight additives may be effective, such additives are less preferred, as cost is increased, and further may result in thickening and foaming of the solution, which requires greater expenditures of time and care during the manufacturing process. Example 14 uses monomeric 4-vinylbenzenesulfonic acid, and Example 21 employs the polymerized analog polystyrenesulfonic acid at an equivalent absolute amount. The polymeric version (Example 21) yielded a much smaller grain size, whereas the lower molecular weight monomer (Example 14) gave only a modest grain size reduction, likely requiring a greater amount to be added to be effective.

In accordance with preferred embodiments, the best combination of benefits from the additives of the invention (e.g. reduced grain size, grain size distribution, and discoloration)

have been demonstrated with the use of sodium dodecyl-sulfate and polystyrenesulfonic acid additives.

Examples 22-23

Preparation of Polypropylene Plaques, Strands and Films

Polypropylene plaques, strands and films were prepared, with and without silver sulfate additives.

Example 22A

Comparative Composite (No Silver Sulfate)

Into a glass vessel was charged 20 grams of polypropylene (Huntsman 4C6Z-022). The vessel was then placed on a Corning PC-35 Hotplate set at heat setting 5. The polypropylene was heated until visually melted then stirred with a stainless steel spatula. The melted polypropylene was removed from the glass vessel using the spatula and placed on a Teflon sheet and allowed to cool to room temperature (23° C.), giving a solid plaque. All melting and cooling steps occurred in ambient air. The color of the solid plaque was white and served as a comparison for color for all composite examples associated with this invention.

Example 22B

Comparative Composite (Commercial Silver Sulfate)

Into a glass vessel was charged 20 grams of polypropylene (Huntsman 4C6Z-022). The vessel was then placed on a Corning PC-35 Hotplate set at heat setting 5. The polypropylene was heated until visually melted. One gram of commercial silver sulfate (Riverside Chemical) that had been previously ball-milled to a size of less than 50 micrometers was added to the melted polypropylene in the glass vessel. The silver sulfate and polypropylene mixture was then stirred with a stainless steel spatula for 2 minutes. During this mixing step, the color of the mixture turned brown. The resulting composite was removed from the glass vessel using the spatula and placed on a Teflon sheet and allowed to cool to room temperature (23° C.), giving a solid plaque. All mixing, melting and cooling steps occurred in ambient air. The color of the solid plaque was brown indicating that mixing of this commercially available silver sulfate with polypropylene did not allow the making of a white silver sulfate-polypropylene composite.

Example 22C

Comparative Composite (Commercial Silver Sulfate)

A sample of silver sulfate was purchased from Aldrich Chemical Company. The mean grain size for this commercially available material was determined to be 170 μm by light scattering (HORIBA), with the standard deviation of the grain size distribution being 93 μm.

Into a glass vessel was charged 20 grams of polypropylene (Huntsman 4G2Z-159). The vessel was then placed on a Corning PC-35 Hotplate set at heat setting 5. The polypropylene was heated until visually melted. One gram of silver sulfate (Aldrich Chemical) was added to the melted polypropylene in the glass vessel. The silver sulfate and polypropylene mixture was then stirred with a stainless steel spatula for 2 minutes. During this mixing step, the color of the mixture turned brown. The resulting composite was removed from the glass vessel using the spatula and placed on a Teflon sheet and allowed to cool to room temperature (23° C.), giving a solid plaque. All mixing, melting and cooling steps occurred in ambient air. The color of the solid plaque was brown indicating that mixing of this commercially available silver sulfate with polypropylene did not allow the making of a white silver sulfate-polypropylene composite.

Example 22D

Comparative Composite (Ex. 2 Silver Sulfate, No Additive)

A Brabender compounder was preheated to 232° C. Into the Brabender mixing chamber was charged 36 grams of polypropylene (Huntsman 4G2Z-159). The polypropylene melted and was then compounded for 2 minutes. Four grams of silver sulfate as prepared in Example 2 (no additive) was added to the mixing chamber and compounded with the melted polypropylene for 5 minutes. The resulting composite was removed from the Brabender using a spatula and placed on a steel plate and allowed to cool to room temperature (23° C.), giving a solid plaque. Melting and mixing steps occurred in a nitrogen ambient, cooling occurred in ambient air. The color of the solid plaque was brown indicating that mixing of this comparative silver sulfate (no additive) with polypropylene did not allow the making of a white silver sulfate-polypropylene composite.

Example 22E

Comparative Composite (Riverside Chem in PolyLab Strand)

Into a plastic bag was charged 950 grams of polypropylene (Huntsman 4C6Z-022) and 50 grams of a commercially available silver sulfate (Riverside Chemical). The polypropylene pellets and silver sulfate powder were mixed in the plastic bag for 5 minutes, and then added to a Ktron SCM feeder. The feeder was positioned to feed the polypropylene and silver sulfate mixture into zone 1 of a PolyLab twin-screw compounder at a feed rate of 4 pounds per hour. The extruder barrel was preheated to 400° F., and the screw rpm was set at 400. All mixing, melting and cooling steps occurred in ambient air. The resulting composite was extruded as a brown strand and quenched to room temperature (22° C.) in a stationary water bath. The resulting solid strand was brown indicating that mixing of this commercially available silver sulfate with polypropylene did not allow the making of a white silver sulfate-polypropylene composite.

Example 22F

Inventive Composite (Ex. 16B Silver Sulfate, SDS Additive)

Into a glass vessel was charged 20 grams of polypropylene (Huntsman 4C6Z-022). The vessel was then placed on a Corning PC-35 Hotplate set at heat setting 5. The polypropylene was heated until visually melted. One gram of silver sulfate precipitated with additive sodium dodecylsulfate as described in Example 16B above, was added to the melted polypropylene in the glass vessel. The silver sulfate and polypropylene mixture was then stirred with a stainless steel spatula for 2 minutes. During this mixing step, the color of the mixture was white. The resulting composite was removed from the glass vessel using the spatula and placed on a Teflon sheet and allowed to cool to room temperature (23° C.), giving a solid plaque. All mixing, melting and cooling steps occurred in ambient air. The color of the solid plaque was white indicating that mixing of this inventive silver sulfate with polypropylene allowed the making of a white silver sulfate-polypropylene composite. This result is unexpected because all comparative silver sulfate and polypropylene composites are brown in color. No additional additives were required to preserve the white color of the composite over a several week period.

Example 22G, Inventive Composite (Ex. 16B Silver Sulfate, SDS Additive)

The procedure of Example 22F was repeated, except with Huntsman 4G2Z-159 grade polypropylene. One gram of inventive silver sulfate made in Example 16B (sodium dodecylsulfate additive) was used once again. The color of the solid plaque was once more white indicating that mixing of this inventive silver sulfate with polypropylene allowed the making of a white silver sulfate-polypropylene composite. This result is unexpected because all comparative silver sulfate and polypropylene composites are brown in color. Similarly, no additional additives were required to preserve the white color of the composite during several weeks of observation.

Example 22H, Inventive Composite (Ex. 16B Silver Sulfate, SDS Additive in Brabender)

The procedure of comparative Example 22D employing a Brabender compounder was repeated except that two grams of inventive silver sulfate as prepared in Example 16B (sodium dodecylsulfate additive) was added to the mixing chamber and compounded with the melted polypropylene. The color of the resulting solid plaque was white indicating that mixing of this inventive silver sulfate with polypropylene by this procedure allowed the making of a white silver sulfate-polypropylene composite. This result is unexpected because all comparative silver sulfate and polypropylene composites are brown in color. The plaque remained white in color over several weeks of observation without the aid of any other color-preserving additives.

Example 22I, Inventive Composite (Ex. 16B Silver Sulfate, SDS Additive in PolyLab Strand)

A plastic bag was charged with 950 grams of polypropylene (Huntsman 4C6Z-022) and 50 grams of inventive silver sulfate as prepared in Example 16B (sodium dodecylsulfate additive). The polypropylene pellets and inventive silver sulfate powder were mixed in the plastic bag for 5 minutes, and then added to a Ktron SCM feeder. The feeder was positioned to feed the polypropylene and silver sulfate mixture into zone 1 of a PolyLab twin-screw compounder at a feed rate of 4 pounds per hour. The extruder barrel was preheated to 330° F., and the screw rpm was set at 400. All mixing, melting and cooling steps occurred in ambient air. The resulting composite was extruded as a white strand and quenched to room temperature (22° C.) in a stationary water bath. The resulting solid strand was white indicating that mixing of this inventive silver sulfate with polypropylene allowed the making of a white silver sulfate-polypropylene composite strand. This result is unexpected because all comparative silver sulfate and polypropylene composites are brown in color. The extruded strands remained white in color over several weeks of observation without the aid of any other color-preserving additives.

A summary of the thermal stability results for the plaque samples of Examples 22A-22I is contained in Table 2 below.

TABLE 2

| Ex. | Equipment | PP source (Huntsman) | Silver Sulfate Source | Amount (wt. %) | Plaque Color | Example Type |
|-----|-----------|----------------------|-----------------------|----------------|--------------|--------------|
| 22A | Beaker | 4C6Z-022 | None | — | White | Comp. |
| 22B | Beaker | 4C6Z-022 | Riverside Chem | 5% | Brown | Comp. |
| 22C | Beaker | 4G2Z-159 | Aldrich Chem | 5% | Brown | Comp. |
| 22D | Brabender | 4G2Z-159 | Example 2 | 10% | Brown | Comp. |
| 22E | PolyLab | 4C6Z-022 | Riverside Chem | 5% | Brown | Comp. |
| 22F | Beaker | 4C6Z-022 | Example 16B | 5% | White | Inv. |
| 22G | Beaker | 4G2Z-159 | Example 16B | 5% | White | Inv. |
| 22H | Brabender | 4G2Z-159 | Example 16B | 5% | White | Inv. |
| 22I | PolyLab | 4C6Z-022 | Example 16B | 5% | White | Inv. |

The results shown above for Examples 22B-22E illustrate the discoloration problem commonly encountered for polymer compounded with silver sulfate materials obtained commercially or precipitated in the absence of an additive of the invention. In contrast, Examples 22F-22I that employ silver sulfate prepared with an additive in accordance with the invention display a white color matching that of similarly processed polypropylene (Example 22A) that did not contain silver sulfate.

Example 23, Inventive Composite (Ex. 16B Silver Sulfate, SDS Additive in PolyLab Film)

The procedures of Example 22I employing silver sulfate prepared in Example 16B were repeated, with the exception that the amount of silver sulfate was 0.5% by weight and a die was attached to the exit of the PolyLab twin-screw compounder such that films of roughly 15 cm width by 50-75 µm thickness were extruded. This composite film was examined by optical microscopy. The particles of silver sulfate were well dispersed, and the median size judged to be about 7 µm with a maximum observed size of about 10 µm. Comparison films without silver sulfate were also prepared by these same methods.

Composite films of polypropylene and silver sulfate of the invention were evaluated for antimicrobial activity using modifications of ASTM E-2180, "Standard Test Method for Determining the Activity of Incorporated Antimicrobial Agent(s) in Polymeric or Hydrophobic Materials." In this test, extruded plastic samples (with and without incorporated antimicrobial silver species) were cut into strips of 4.5 cm by 2.0 cm for a total surface area of 18 cm$^2$. The sample strips were wiped down with alcohol to remove any handling contamination and residual debris or bacteria, and placed into glass tubes. The strips were inoculated with organisms ($10^4$ cells/milliliter), using bacteria (*Staphylococcus aureus* (ATCC #6538) or *Klebsiella pnuemoniae* (ATCC #4352)) or fungi (*Aspergillus niger* (ATCC #6275)). For bacteria, inoculation was carried out along with 1% (by volume) triptocase soy broth (TSB) nutrient, the strips were incubated for 24 hours at 35° C., then the organisms were removed from the strips by vortexing and filter plated onto triptocase soy agar (TSA), and then incubated for another 48 hours at 35° C. After this final incubation, the filter plates were examined for bacterial growth and the colonies were counted. For fungi, the strips were incubated for 4 and 7 days at 28° C. in 1% (by volume) Sabourand dextrose broth (SDB), then the organisms were removed from the strips by vortexing and filter plated onto Sabouraud dextrose agar (SDA) and incubated for another 7 days at 28° C. Following this final incubation, the filter plates were examined for fungal growth and the colonies counts recorded.

Antimicrobial test results for Example 23 and comparison (blank) films for *Staphylococcus aureus* and *Aspergillus niger* reported in terms of colony forming units per milliliter of inoculant solution (CFU/ml) are contained in Table 3 below.

TABLE 3

| Film | Staph. Aureus: 24 hr contact/ 48 hr incubation | Aspergillus niger: 4 day contact/ 7 day incubation | Aspergillus niger: 7 day contact/ 7 day incubation |
| --- | --- | --- | --- |
| Blank | 2100 | 280 | 200 |
| Example 23 | 20 | <10 | <10 |

Results above showing reduced counts clearly demonstrate that composite films of polypropylene and silver sulfate of the invention possess bactericidal and fungicidal properties.

The invention has been described in detail with particular reference to certain preferred embodiments thereof, but it will be understood that variations and modifications can be effected within the spirit and scope of the invention.

The invention claimed is:

1. A process comprising reacting an aqueous soluble silver salt and an aqueous soluble source of inorganic sulfate ion in an agitated precipitation reactor vessel and precipitating particles comprising primarily silver sulfate, wherein the reaction and precipitation are performed in the presence of an aqueous soluble organo-sulfate or organo-sulfonate additive compound, the amount of additive being a minor molar percentage, relative to the molar amount of silver sulfate precipitated, and effective to result in precipitation of particles comprising primarily silver sulfate of a grain size smaller than that obtained in the absence of the organo-sulfate or organo-sulfonate additive compound and having a mean grain size of less than 50 micrometers.

2. A process according to claim 1, wherein the amount of additive present during the precipitation is less than 20 molar percent, relative to the molar amount of silver sulfate precipitated.

3. A process according to claim 1, wherein the amount of additive present during the precipitation is less than 10 molar percent, relative to the molar amount of silver sulfate precipitated.

4. A process according to claim 1, wherein the amount of additive present during the precipitation is at least 0.01 molar percent, relative to the molar amount of silver sulfate precipitated.

5. A process according to claim 1, wherein the additive compound comprises an organic moiety containing greater than 8 carbon atoms.

6. A process according to claim 1, wherein the additive compound comprises 8 or less carbon atoms.

7. A process according to claim 6, wherein the amount of additive present during the precipitation is at least 5 molar percent, relative to the molar amount of silver sulfate precipitated.

8. A process according to claim 1, wherein the additive compound comprises an alkyl sulfate or alkyl sulfonate compound.

9. A process according to claim 8, wherein the additive compound comprises an alkyl group containing greater than 8 carbon atoms.

10. A process according to claim 9, wherein the additive compound comprises a dodecyl sulfate compound.

11. A process according to claim 1, wherein the additive compound comprises a sulfonated polymer compound.

12. A process according to claim 1, wherein the additive compound has an aqueous solubility of at least 1 g/L.

13. A process according to claim 1, wherein the soluble silver salt comprises silver nitrate, and the soluble source of inorganic sulfate ion comprises sulfuric acid, sodium sulfate, or ammonium sulfate.

14. A composition of matter comprising particles of primarily silver sulfate, where the particles have a mean grain size of less than 50 micrometers and comprise a minor molar amount of an organo-sulfate or organo-sulfonate additive relative to the molar amount of silver sulfate.

15. A composition according to claim 14, wherein the particles have a mean grain size of less than 20 micrometers.

16. A composite comprising a thermoplastic polymer phase and particles of the composition of claim 14 dispersed therein.

17. A composite according to claim 16, wherein the thermoplastic polymer phase comprises a polyolefin.

18. A composite according to claim 17, wherein the thermoplastic polymer phase comprises a polypropylene.

19. A composite according to claim 16, wherein the particles of primarily silver sulfate have a mean grain size of less than 20 micrometers.

20. A composite according to claim 16, wherein the polymer phase is in the form of an extruded film or fiber.

* * * * *